(12) United States Patent
Lapotko et al.

(10) Patent No.: US 7,230,708 B2
(45) Date of Patent: Jun. 12, 2007

(54) METHOD AND DEVICE FOR PHOTOTHERMAL EXAMINATION OF MICROINHOMOGENEITIES

(76) Inventors: Dmitri Olegovich Lapotko, Berestyanskaya str, 26-28, 220071, Minsk (BY); Vladimir Paulovich Zharov, 13605 Longtree Dr., Little Rock, AR (US) 72223

( * ) Notice: Subject to any disclaimer, the term of this patent is extended or adjusted under 35 U.S.C. 154(b) by 437 days.

(21) Appl. No.: 10/465,981

(22) PCT Filed: Dec. 27, 2001

(86) PCT No.: PCT/BY01/00017

§ 371 (c)(1),
(2), (4) Date: Nov. 26, 2003

(87) PCT Pub. No.: WO00/005046

PCT Pub. Date: Jul. 11, 2002

(65) Prior Publication Data

US 2004/0085540 A1    May 6, 2004

(30) Foreign Application Priority Data

Dec. 28, 2000    (BY)    .............................. a 20001187

(51) Int. Cl.
*G01N 21/00*    (2006.01)

(52) U.S. Cl. ...................................... 356/432

(58) Field of Classification Search .................. None
See application file for complete search history.

(56) References Cited

U.S. PATENT DOCUMENTS 4,239,040 A    12/1980    Hosoya et al.

(Continued)

FOREIGN PATENT DOCUMENTS

RU    2000/132985/14    11/2002

(Continued)

OTHER PUBLICATIONS

American Society for Laser Medicine and Surgery Abstracts, Lasers in Surgery and Medicine, The Official Journal of the American Society for Laser Medicine and Surgery, Inc., American Society for Laser Medicine and Surgery 23rd Annual Meeting, Supplement 15, 2003, Wiley-Liss, Apr. 9-13, 2003, pp. 44 and 46.

(Continued)

*Primary Examiner*—Michael P. Stafira
(74) *Attorney, Agent, or Firm*—Speed Law Firm; Kyla D. Cummings; Gary N. Speed

(57) ABSTRACT

The invention relates to optical microscopy, and more particularly to the methods for photothermal examination of absorbing microheterogeneities using laser radiation. The invention can be widely used in laser technique, industry, and biomedicine to examine transparent objects with absorbing submicron fragments, including detection of local impurities and defects in super-pure optical and semiconducting materials and non-destructive diagnostics of biological samples on cellular and subcellular levels.

The object of the present invention is to increase sensitivity, spatial resolution and informative worth when examining local absorbing heterogeneities in transparent objects, as well as to detect the size of said heterogeneities even if said size is smaller than the radiation wavelength used.

Said object is achieved by the pump beam irradiation of a sample, the duration of said irradiation not being longer than the characteristic time of cooling of the microheterogeneity observed. A relatively vast surface of the sample is irradiated at once, the size of said surface not being larger than the wavelength of the pump laser used. The refraction index thermal variations, induced by the pump beam in the sample and being the result of absorption, are registered by the parameter change of the probe laser beam. A chosen probe beam diameter should not be smaller than the pump beam diameter. The diffraction-limited phase distribution over the probe laser beam cross-section is transformed to an amplitude image using a phase contrast method. The properties of microheterogeneities are estimated by measuring said amplitude image.

29 Claims, 9 Drawing Sheets

U.S. PATENT DOCUMENTS

| | | | |
|---|---|---|---|
| 4,750,822 A * | 6/1988 | Rosencwaig et al. | 356/445 |
| 4,930,504 A | 6/1990 | Diamantopoulos et al. | |
| 5,259,380 A | 11/1993 | Mendes et al. | |
| 5,278,432 A | 1/1994 | Ignatius et al. | |
| 5,339,223 A | 8/1994 | Kremenchugsky et al. | |
| 5,358,503 A | 10/1994 | Bertwell et al. | |
| 5,365,065 A | 11/1994 | Power | |
| 5,408,327 A | 4/1995 | Geiler et al. | |
| 5,445,608 A | 8/1995 | Chen et al. | |
| 5,489,279 A | 2/1996 | Meserol | |
| 5,549,660 A | 8/1996 | Mendes et al. | |
| 5,571,151 A | 11/1996 | Chen et al. | |
| 5,616,140 A | 4/1997 | Prescott | |
| 5,660,461 A | 8/1997 | Ignatius et al. | |
| 5,698,866 A | 12/1997 | Doiron et al. | |
| 5,728,090 A | 3/1998 | Martin et al. | |
| 5,748,317 A * | 5/1998 | Maris et al. | 356/502 |
| 5,766,222 A | 6/1998 | Petit | |
| 5,766,234 A | 6/1998 | Chen et al. | |
| 5,781,294 A | 7/1998 | Nakata et al. | |
| 5,845,640 A | 12/1998 | Lawandy | |
| 5,913,883 A | 6/1999 | Alexander et al. | |
| 6,045,575 A | 4/2000 | Rosen et al. | |
| 6,096,066 A | 8/2000 | Chen et al. | |
| 6,206,873 B1 | 3/2001 | Paolini et al. | |
| 6,268,916 B1 * | 7/2001 | Lee et al. | 356/369 |
| 6,290,713 B1 | 9/2001 | Russell | |
| 6,443,978 B1 | 9/2002 | Zharov | |
| 6,504,618 B2 * | 1/2003 | Morath et al. | 356/630 |

FOREIGN PATENT DOCUMENTS

| | | |
|---|---|---|
| RU | 2203112 C2 | 4/2003 |
| WO | WO 02/053224 | 7/2002 |
| WO | WO 03/014770 | 2/2003 |

OTHER PUBLICATIONS

American Society for Laser Medicine and Surgery Abstracts, Lasers in Surgery and Medicine, The Official Journal of the American Society for Laser Medicine and Surgery, Inc., Lasers 2001, American Society for Laser Medicine and Surgery 21st Annual Meeting, Supplement 13, 2001, Wiley-Liss, Apr. 20-22, 2001, pages 6 and 30.

Zharov, Vladimir P. et al., Phototherapeutic Treatment of Patients with Peripheral Nervous System diseases by Means of LED Arrays, Lasers in Surgery: Advanced Characterization, Therapeutics, and Systems XI, R, Rox Anderson et al. (editors), Proceedings of SPIE, vol. 4244, 2001, pp. 143-147.

Lapotko, Dmitry et al., Photothermal Image Cytometry of Human Neutrophils, Cytometry, vol. 24, pp. 198-203, Wiley-Liss, Nov. 8, 1995.

Letokhov, V.S., Effects of Transient Local Heating of Spatially and Spectrally Heterogeneous Biotissue by Short Laser Pulses, II Nuovo Cimento, Feb. 21, 1991, vol. 13 D, No. 7, pp. 939-948.

Zharov, Vladimir et al., Photothermal Sensing of Nanoscale Targets, Review of Scientific Instruments, Proceedings of the 12th International Conference of Photoacoustic and Photothermal Phenomena Jun. 24-27, 2002, Toronto, Ontario, Canada, vol. 71, No. 1, Jan. 2003, Part II, pp. 785-788.

Lapotko, Dmitri et al., Photothermal Images of Live Cells in Presence of Drug, Journal of Biomedical Optics, vol. 7, No. 3, Jul. 2002, pp. 425-434.

Lapotko, Dmitri et al., Photothermal Time-Resolved Imaging of Live Cells, Lasers in Surgery and Medicine, Wiley-Liss, vol. 31, 2002, pp. 53-63.

Galanzha, Ekateryna I. et al., The Diagnosis of Lymph Microcirculation in Experimental Studies on Rat Mesentery in Vivo, Optical Diagnostics and Sensing in Biomedicine III, Proceedings of the SPIE, The International Society of Optical Engineering, vol. 4965, pp. 55-65, Jul. 2003.

* cited by examiner a) b) c)

a) b)

METHOD AND DEVICE FOR PHOTOTHERMAL EXAMINATION OF MICROINHOMOGENEITIES

This is a 371 application of International Application No. PCT/BY01/00017, filed Dec. 27, 2001, which claims priority from Belarus Patent Application No. a20001187 filed Dec. 28, 2000.

TECHNICAL FIELD

The invention relates to optical microscopy, and more particularly to the methods for photothermal (PT) examination of absorbing microheterogeneities using laser radiation, and can be widely used to examine transparent objects with absorbing submicron fragments in laser technique, industry, and biomedicine, including detection of local impurities and defects in super-pure optical and semiconducting materials and non-destructive diagnostics of biological samples on cellular and sub-cellular levels.

TECHNICAL LEVEL

There are known numerous methods for optical examination of microheterogeneities using optical microscopes of various modifications, including methods with the use of lasers. In the general, said methods and the corresponding devices have a diffraction limit on resolution or allow examining the object's image by high spatial resolution right up to separate molecules, but as a rule, only on the surface of solid samples. Thus, said methods and devices cannot be used effectively to examine optically transparent objects, including biological samples in the form of live cells placed in suspension.

The greatest refraction index sensitivity is realized in phase microscopes to examine optically transparent objects, including phase contrast schemes and laser interference microscopes [1]. However, said microscopes have low sensitivity to analyze low absorption.

The increase of the microscope absorption sensitivity is possible in laser calorimetric methods, wherein thermal and acoustic phenomena resulting from non-radiation relaxation of the absorbed energy are the source of the signal. More particularly, thermal effects can be registered using an additional (probe) laser beam. Parameters of said laser beam (angle of deflection, phase, and amplitude) are measured as the function of the refraction index change of the object observed. For example, the degree of the probe laser beam defocusing is registered by a thermal lens method. Deflection methods are based on the deflection analysis of the probe laser beam (or its reflection from the surface of the object observed). Beside diffraction limit on resolution (about 1 μm), the shortcoming of said method is laser beam scanning on the surface of the object observed, that takes much time. In fact, such methods allow detecting absorption from submicron zones, but they do not allow obtaining information concerning the size of said zones.

The existing photothermal method and apparatus for the surface and subsurface information analysis of the object are well-known, wherein the surface of the object observed is irradiated by a pump laser beam (continuous, with a certain frequency and amplitude modulation) in various points simultaneously, and also by a focused probe laser beam in the same points [2]. The phenomenon of the object's surface displacement due to its absorption heating is used in this method. As a result, a two-dimensional amplitude image of the thermally induced surface displacement is obtained without scanning the object's surface. This method is successfully used to detect crystalline defects in semiconducting devices, crystalline defects of laser optics, and optical heterogeneities. The apparatus for implementation of this method is the closest analogue to the apparatus claimed, and it comprises two lasers: a continuous modulated pump laser and a continuous probe laser, and a number of photodetectors corresponding to each point of the object observed. However, said device is designed to examine only a solid reflecting surface. Besides, spatial resolution of said method couldn't be better than the diffraction limit.

The method for laser examination of absorbing heterogeneities in relatively transparent objects, described in the work [3], is the closest method to the one claimed, and it is partially free from said shortcomings. In said method laser pulse is used to provide short-term heating of the absorbing zones of submicron size and examination of their spectral properties before quick cooling of said zones. To register these, it is suggested that laser pulse scattering of the second laser should be registered on refraction heterogeneities influenced by the absorption force of the first laser beam. It is also noted that fluorescent radiation from the heated zone or fluorescence induced by the second laser could be registered. The main shortcoming of said method is its low sensitivity because of the non-optimal methods for registering local heat variations of the refraction index. Another shortcoming is that only one heterogeneity can be examined, i.e., the discussed method and the described scheme do not allow obtaining simultaneous image of a number of heterogeneities in the irradiation volume. And finally, there's no opportunity for measuring the sizes of separate heterogeneities and there are no corresponding methods for quantitative estimation of said sizes.

THE OBJECT AND SUMMARY OF THE INVENTION

The object of the present invention is to eliminate all said shortcomings, i.e. to increase sensitivity, spatial resolution and informative worth when examining local absorbing heterogeneities in transparent objects, as well as to determine the size of said heterogeneities even if it is smaller than the radiation wavelength used. More particularly, one of the main objects of the invention is to develop method and apparatus for obtaining image of the whole object, to provide examination of a number of submicron heterogeneities simultaneously, including method for determination their size and sensitivity to various external conditions, and to radiation and temperature in particular.

To solve the problem, a relatively large sample surface is exposed to the pump laser radiation. The size of said surface exceeds the wavelength of the pump laser beam used. In fact, surface of any size could be irradiated, but logically, said size could not exceed the size of the sample itself. The chosen probe laser beam diameter not being smaller or being comparable with the pump laser beam diameter, and not being larger than the maximum overall dimensions of the sample. Spatial distribution of absorbing heterogeneities in the irradiation zone is determined by the synchronous measurement of the diffraction limited phase distribution through the whole cross-section of the probe laser beam which is transformed into an amplitude image by a phase contrast method. The size of separate microheterogeneities larger than the pump laser beam wavelength is determined by analyzing said amplitude image structure. The amplitude image corresponds to the refraction index change distribution induced by the pump laser in the object observed. And the average size of microheterogeneities smaller than the wavelength is measured indirectly, by the characteristic time of cooling that depends on the size. Said measurement is accomplished on the basis of the rate of change of the phase of diffraction-limited images of said microheterogeneities in various points of the probe laser beam cross-section at different moments of time, commencing right after pump laser irradiation has taken place, the chosen irradiation period being much shorter than the characteristic time of cooling of the microheterogeneity observed. A short-time irradiation can be performed by two methods. The first method uses a single laser pulse. It is the duration of said pulse that determines the period of impact. A pulse-periodic mode, usually with porosity more than 1, could also provide said effect. Another opportunity is using continuous laser pump radiation that is intensity-modulated with a relatively high modulation frequency ranged from a few kHz to hundreds of MHz. In this case duration of a single effect is determined by a modulation semi-period. Said effect repeats with the frequency determined by the laser modulation frequency. In this case information about the time of cooling would be carried by the probe laser beam time phase related to the pump laser beam time phase.

A number of versions of the probe beam realization could be used. For example, a part of the pump laser beam could be used as a probe beam. Propagating the probe beam through an additional optical delay line regulates its delay time as related to the main beam. The chosen probe beam intensity should be considerably (at least 5–10 times) lower than the main beam intensity, so as to have minimal effect on the measurement results.

According to the aforesaid, the size of microheterogeneities is determined by comparing the probe beam phase in separate points measured by various time delays.

Pulse radiation of the second independent laser could be used as a probe beam. Time delay is to be regulated as related to the pump laser pulse. According to said scheme, the easiest method to be used when having one pump pulse is to measure the phase with one time delay. A number of pump pulses are to be used to measure phases with various time delays.

Continuos wave of the second independent laser could also be used as a probe laser beam. In this case said phase distribution is registered in the time delay function from the beginning of the pump pulse. In this connection, beginning of the probe beam phase monitoring is to be synchronized with the beginning of the pump laser pulse effect.

It is suggested that information about the heterogeneities distribution on the sample surface having the sizes not larger than the pump beam diameter, should be obtained by the consecutive change of said amplitude image in various sample zones that are away from one another at a distance equal to the pump beam diameter. The easiest transition from one zone to another could be accomplished using relative shift of the sample and both said beams.

Coaxial geometry of the probe and the pump beams is the most reasonable and easy when irradiating the object observed. One of its advantages is non-criticality to possible optical misalignments of both beams.

However, various spatial orientations of both beams (also the one at an angle to each other) are possible, including reciprocally orthogonal geometry.

Said phase distribution of the probe laser beam in the function of the pump laser wavelength should be measured, so as to obtain information about spectral properties of separate microheterogeneities simultaneously with their sizes. It is suggested that said measurement is to be accomplished by at least two time delays as related to the pump beam pulse at every pump laser wavelength.

Information about non-linear optical properties of separate absorbing heterogeneities right up to irreversible change of their parameters induced by the pump beam should be obtained when irradiating the sample by a number of pump laser pulses having equal wavelength and duration. But said pulses have consecutively increasing radiation intensity and registration of maximum amplitude and time form of the phase change of the continuous probe beam, commencing from the moment the pump beam begins operating. Thus, dependence of the absorbed energy on radiation intensity is obtained. The slope of said dependence determines absorption character in separate microheterogeneities. For example, sensitivity limit of the present method, that is proportional to the pump pulse energy in the linear mode, is determined by shifting from linear dependence to saturation. Quadratic dependence will be indicative of two-photon absorption, and a bigger slope will be indicative of multi-photon absorption.

It is suggested that information about longitudinal distribution of heterogeneities along the pump beam optical axis should be obtained by consecutive measurement of the probe laser beam phase distribution by different mutual relative orientations of the probe laser beam and the object observed. For example, it could be achieved by a relative turn of the sample and the probe laser beam; by turning the two beams as related to each other and the sample, etc. A three-dimensional distribution is then restored using Radon's theorem and corresponding tomography calculating methods.

The deflection degree of the probe beam space-time phase distribution should be measured in process and after external effect is over, as compared to the initial distribution immediately before the external effect begins. Said measurement is to be accomplished to estimate influence of the external impacts on the sample, such as physical and/or chemical and/or biological factors, e.g., ionizing radiation, temperature, pressure, chemical substances (drug) in case biological samples are analyzed. The change of various properties of microheterogeneities, induced by the external effect, should be used as one of the sensitive indicators of said effect, including thermal response to the pump laser test effect. The size of the microheterogeneities is to be smaller than the pump laser wavelength (optical, thermal, geometrical, etc.).

Dynamic change of said microheterogeneities, induced by the pump beam, should be examined by changing at least two phase images, one of which is obtained immediately before the pump pulse operation, and the others are obtained simultaneously with the pulse or with a delay, with their subsequent subtraction. It is particularly important in case there are insignificant alterations of the image structure, that are difficult to identify using only one image, as the measurement precision is low.

One of the claimed algorithms for determination of the average size of absorbing microheterogeneities is alteration of the probe beam phase at the spot of the heterogeneity's location in two moments of time $t_1$ and $t_2$, after the pump pulse is over. The average radius of the heterogeneity is then calculated according to the following formula:

$$R=[4k((S_1/S_2)^{2/3}t_1-t_2)/(1-(S_1/S_2)^{2/3})]^{0.5} \qquad (1),$$

Where $t_1$ and $t_2$ are the moments of time, $S_1$ and $S_2$ are the values of the photothermal signal amplitude at the moments of time $t_1$ and $t_2$, k is the thermal conductivity coefficient of the cell's environment.

To accomplish the present method, an additional optical system of phase contrast is used as an optical transformation unit to transform phase distribution in the probe beam cross-section to an amplitude image. A registration unit is a high-speed multi-channel photodetector (CCD-matrixes, etc.) in the pulse mode, so as to register said amplitude image of the probe beam at various moments of time as related to the moment of the pump laser pulse operation. Another version of the registration unit is a number of one-channel photodetectors used to register time amplitude changes for one or several zones in said amplitude image of the probe beam. The probe beam falls simultaneously on all the detectors owing to the introduction of a semi-transparent system of mirrors placed on the way of the probe beam behind the phase-contrast system. Another solution is a consecutive spatial shift of said detector using an additional switch unit. To provide examination of the microheterogeneities considerably smaller than the wavelength, the fundamental solution is to introduce a synchronizing unit and a time delay regulating unit connected with each other, with the pump laser units, with the probe laser forming unit, and with the registration unit. It is a gradually regulated delay that allows, when using probe laser and pump laser pulse regimes, obtaining precise measurement of the time of cooling of the absorbing heterogeneities heated by the pump pulse, so as to estimate the average size of said heterogeneities. In case the continuous mode of the probe laser is used, said role is performed by a synchronizing unit that provides the switch of the probe beam phase monitoring at the moment of the pump laser pulse operation.

In the continuous mode of the pump laser and its intensity modulation, the device contains an additional intensity-modulating unit placed on the way of the pump beam distribution. Registration of the continuous probe beam modulation caused by pump radiation (via refraction index modulation) is provided in this case by the synchronous integrating unit connected with a photodetector (or multi-channel photodetectors) of the probe beam. Said unit also receives a signal from the pump beam modulator. The necessary information about the pump laser (time) phase is carried by said signal. The technical embodiment claimed also provides for a one-channel mode, wherein pump radiation accomplishes the probe beam functions simultaneously. In this case phase distribution in the pump beam cross-section itself is registered. The filter cutting the pump beam in front of the photodetector should be removed to follow said scheme.

The system of splitting the pump laser beam into the main one and the additional one is introduced on the way of the pump beam, coming from the pump laser to use part of the pump laser as a probe beam, the additional beam accomplishing the probe beam function. The optical delay line connected with the time delay unit is introduced on the way of the probe beam. A probe beam-forming unit can be realized both as a continuous laser connected with the synchronizing unit and as a pulse laser connected with a time delay unit. A probe beam turning unit should be introduced as related to the sample observed to obtain a three-dimensional tomographic image. Another version is to introduce the turning unit of the sample itself, the former being connected with the synchronizing unit. The device can also be equipped with an image processing unit connected with said photodetectors, the synchronizing unit, and the time delay unit. One of its numerous functions is image comparison at various moments of time, and another one is comparison of photothermal and regular optical images. The device is additionally equipped with a pump beam wavelength-changing unit connected with the pump laser unit. Various methods can be used to provide the laser wavelength change. Said methods include temperature and pressure influence on the active element; using spectral elements within a pump laser resonator in the form of a prism; diffraction grid; interference filters, etc.

Thus the method and apparatus claimed, having a number of fundamental features, are advantageous as compared to the methods already existing. One of the main features is the cooling speed measurement of the absorbing microheterogeneities heated by the pump laser and having the size much smaller than the radiation wavelength used. Said measurement is accomplished by estimation of temporal behavior of the probe beam phase, the probe beam zoning the heterogeneity observed. The advantage of the probe beam phase measurement, as compared, say, to the measurement of its scattering, is a much higher sensitivity. Another significant difference is the possibility to examine absorbing microheterogeneities and determining their sizes over the whole irradiated volume simultaneously. A further advantage is the possibility to obtain a full image of the irradiated volume using one pump laser pulse without scanning. The pump and the probe beam coaxial geometries are highly is non-critical to the mutual location of both beams. Two-dimensional phase image projections using various zoning angles of the probe beam should be measured so as to estimate absorption distribution along the optical axis. It could be achieved by various methods including alteration of the probe beam angle of incidence on the sample or alteration of the angle location of the sample. The easiest solution is alteration of the sample's location, as it allows escaping alignment of the photodetectors' location by every angle location of the probe beam. As a result, two-dimensional projections in various zoning directions of the sample are obtained. According to Radon's theorem, it allows to restore a three-dimensional distribution of absorbing microheterogeneities by the calculating tomography methods. Different modifications of the modes described are possible. For example, in case continuous probe beam radiation is used, its phase image is registered at separate moments of time, said moments corresponding to various delays as related to the pump laser pulse. Instead of the whole image registration, time dependence of the probe beam phase could also be registered in one or several points of the probe beam cross-section using a number of discrete photodetectors. One of the main features of the method claimed is high absorption sensitivity on the level of $10^{-3}$–$10^{-5}$ sm.$^{-1}$, which is impossible using both standard microscopes (including those with laser sources) and phase and confocal microscopes. Upper sensitivity of the method claimed is limited by the maximum possible pump laser energy causing non-linear effects. They are as follows: multi-photon absorption, optical saturation or irreversible changes of the sample properties right up to destruction caused by thermal or accompanied effects (acoustic, mechanical, etc.) Therefore, the yield signal of the photodetector in the linear mode is recommended to keep the linear dependence on the pump energy level. More particularly, it allows eliminating possible influence on the estimation precision of energy instability of the pump laser by fixing the yield signal of the photodetector to the pump laser energy level using analogous or digital schemes. To accomplish said fixing scheme, an additional photodetector should be introduced to register the pump laser energy independently, said photodetector being connected with the dividing unit receiving the useful signal from the photodetectors used in the probe beam channel. The signal fixed to the pump laser energy comes to the image-processing unit after the dividing unit.

The present scheme could also be easily transformed to operate in the reflected light. For example, an additional mirror could be placed immediately behind the object, or a transparent object itself could be placed on said mirror. In case biological objects are analyzed in vivo, e.g. skin, only the probe laser radiation scattered from the upper skin layer could be registered and the temporary kinetics of its phase and amplitude alterations could then be analyzed.

The capability of the device claimed could be extended by the use two-photon and multi-photon effects when absorbing the pump radiation, formed by picosecond and femtosecond lasers in particular. The increase of absorbed photons will be equivalent to the increase of absorption sensitivity of the PT method. Besides, the phase image would be the most sensitive to the zone of the refraction index greatest change along the way of the focused pump laser distribution, i.e. from the caustica zone of the pump beam. More intense focusing of both beams, combined with their spatial scanning, would help increase longitudinal microscope resolution (as an analogue of a multi-photon fluorescence microscopy), said effect allowing more precise identification of the spatial localization zone of absorbing microheterogeneities.

Beside the pulse mode of the pump laser operation, a continuous high-frequency intensity-modulated mode is also claimed, the probe beam modulation induced through the refraction index thermal change being registered using a synchronous detection technique. To perform this, the modulator signal carrying information about the pump beam phase comes to the synchronous detection unit. The average R size of absorbing microheterogeneities is determined by measuring the probe beam time phase as related to the time phase of the intensity-modulated pump beam from the following formula:

$$\tan \phi = \omega \tau_T, \text{ where}$$

$\omega$ is a circular frequency of the pump laser modulation ($\omega = 2\pi f$)

$\tau_T$ is the time of cooling, $$\tau_T = \frac{R^2}{6.75K},$$

where
R is the required radius of the microheterogeneity
K is the thermal diffusivity of the microheterogeneity's environment.

In case a number of heterogeneities having different sizes and, consequently, different time values participate in absorption, they could be selectively registered owing to the choice of the synchronous detector phase coinciding with the signal phase from the corresponding microheterogeneity.

Beside using the phase-contrast method to register thermal effects and the size of absorbing microheterogeneities, other calorimetric methods could be used, and first of all a photothermal radiometry method registering secondary infrared radiation from the microheterogeneities heated by the pump radiation. The advantage of such scheme is its distant character and possibility to control heterogeneities in relatively intensely absorbing objects, e.g., the surface of human skin, when placing laser sources and detectors on one side of the object. Using an additional infrared (IR) optical scheme with a micro-lens and multi-channel IR photodetectors allows obtaining the image of the surface irradiated, and the temporary dynamics analysis of the pulse signal change or the modulated signal phase change according to said algorithms allows obtaining information about the size of absorbing microheterogeneities. Another advantage of said approach is easy combination of said scheme with a confocal reflecting microscope scheme. Using an additional diaphragm in front of the detector would help increase both the regular diffraction limited spatial distribution and especially the longitudinal one. This combination could also be realized using other photo-calorimetric methods including the thermal lens method, said diaphragm possibly performing a double role: providing longitudinal resolution, just as in classical confocal schemes, and intensifying the thermal lens signal from the probe beam defocusing.

In a number of cases additional registration of heating-attendant acoustic effects is useful. This can be accomplished using a high-speed acoustic detector attached to the sample, e.g., on the basis of piezoelectric or pyroelectric structures.

Another method is analysis of a photothermal signal form, corresponding acoustic effects being imposed on said signal. The measurement of the acoustic signal width also allows estimating the size of the corresponding heterogeneity.

BRIEF DESCRIPTION OF THE DRAWINGS

FIG. 1b is a time diagram of the pump laser beam,
FIG. 1c is a time diagram of temperature in the absorbing zone of the object,
FIG. 1d is a time diagram of the probe laser beam phase change in the absorbing zone of the object,
and
FIG. 1e is a time diagram of the photothermal signal in the absorbing zone of the object.
FIG. 7a is an image before the pump laser irradiation.
FIG. 7b and FIG. 7c are images at different moments of time after the pump laser irradiation has taken place.
FIG. 9a is an image before peroxidation.
FIG. 9b is an image after peroxidation of cell membrane lipids.

DETAILED DESCRIPTION OF THE INVENTION AND PREFERRED EXAMPLES

The method discussed is a significant development of the method described in the work [3]. It should once more be emphasized, that the phase contrast method is claimed to be used in the present invention to register light and microheterogeneity interaction, instead of fluorescence detection or light scattering, as in the said work. The phase contrast method is sensitive to the refraction index change induced by a short-time laser effect both in the pump laser pulse mode and in the high-frequency intensity-modulated mode of the continuous pump laser.

Figure 2:
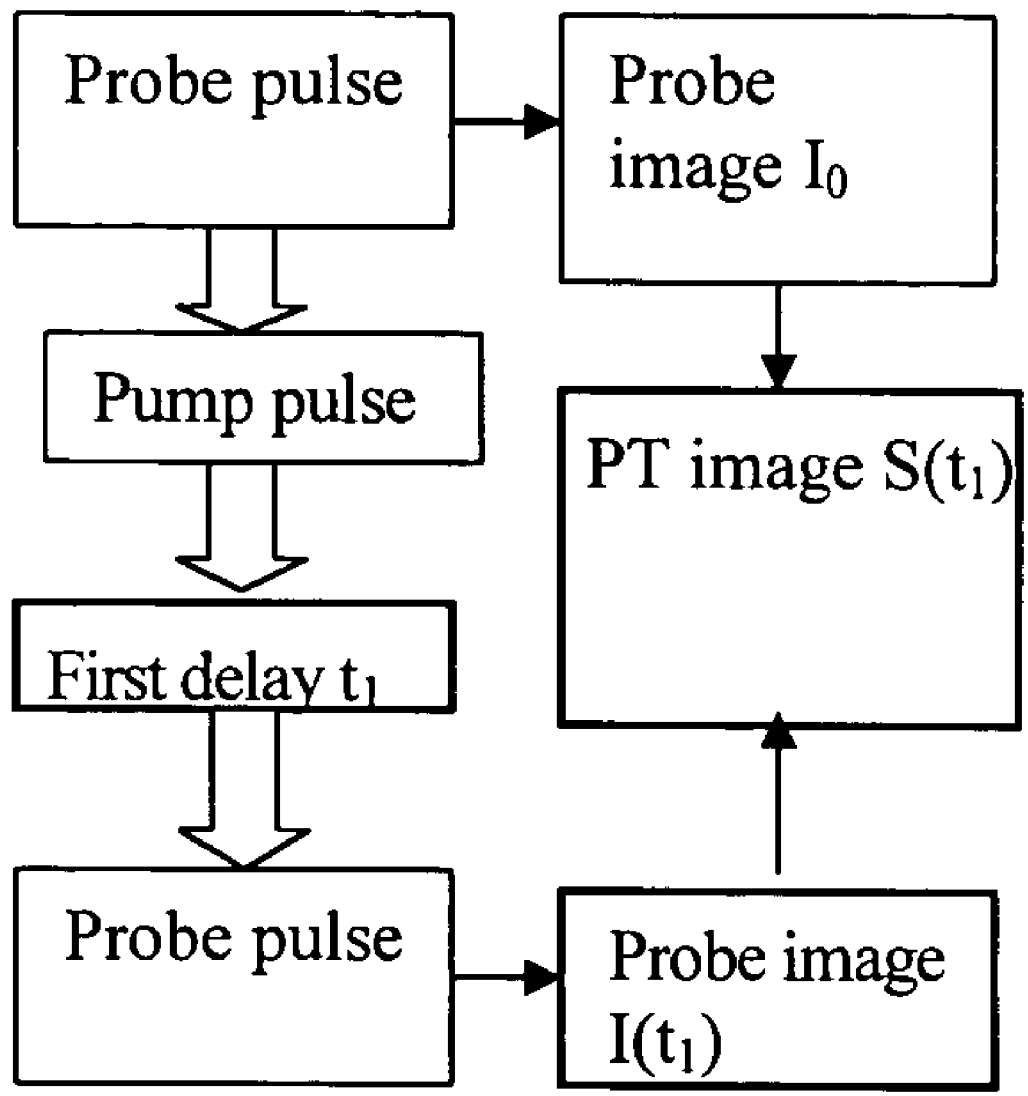
FIG. 2 is an algorithm for obtaining a photothermal image and determining sizes of absorbing microheterogeneities in the object.
Figure 3:
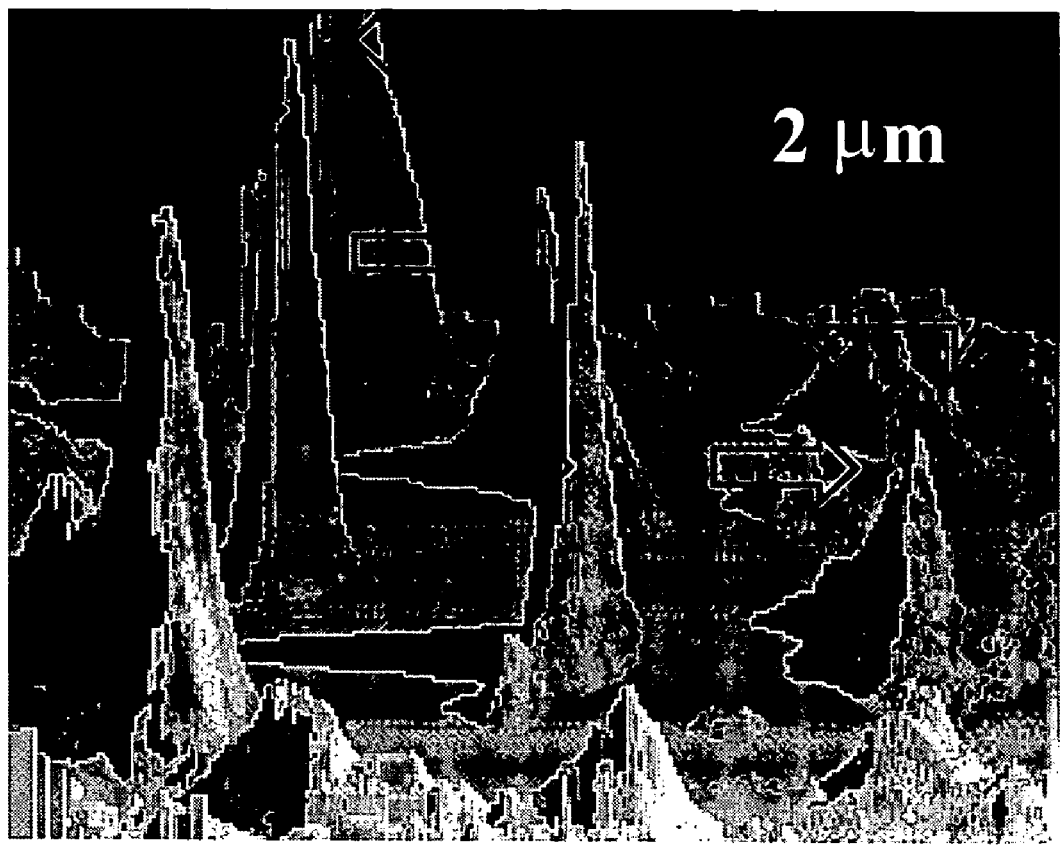
FIG. 3 is an example of a photothermal image of a separate particle—liposome.
Figure 4:
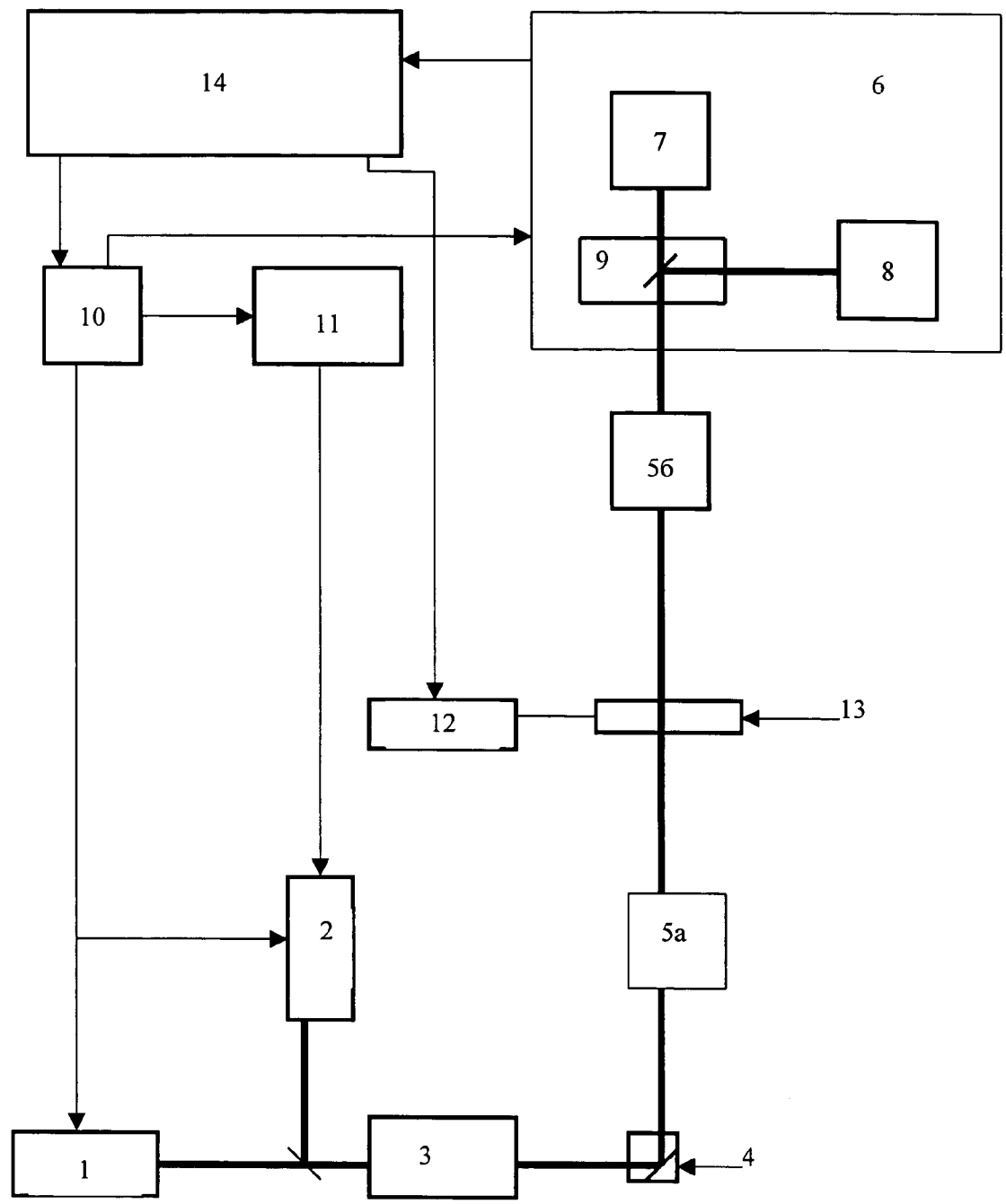
FIG. 4 is a general scheme of the device claimed.

FIG. 2 and FIG. 3 are a general presentation of the claimed method for photothermal examination.

Accomplishing the method begins when the object containing absorbing microheterogeneities is irradiated with a probe laser beam (shown in FIG. 2), the chosen probe beam diameter not being smaller than the pump beam diameter and not being larger than the maximum overall dimensions of the sample. Intensity of the probe beam should be considerably (at least 5–10 times) smaller than the pump beam intensity, so as to cause minimal effect on the measurement results. The diffraction-limited distribution of the probe laser beam phase over the whole cross-section is then transformed to an amplitude image using the phase contrast method. The obtained values of the probe beam phase $\phi_0(x, y)$ and the phase-corresponding amplitude $I_0(x', y')$ of the image are basic for the further analysis.

Figure 1:
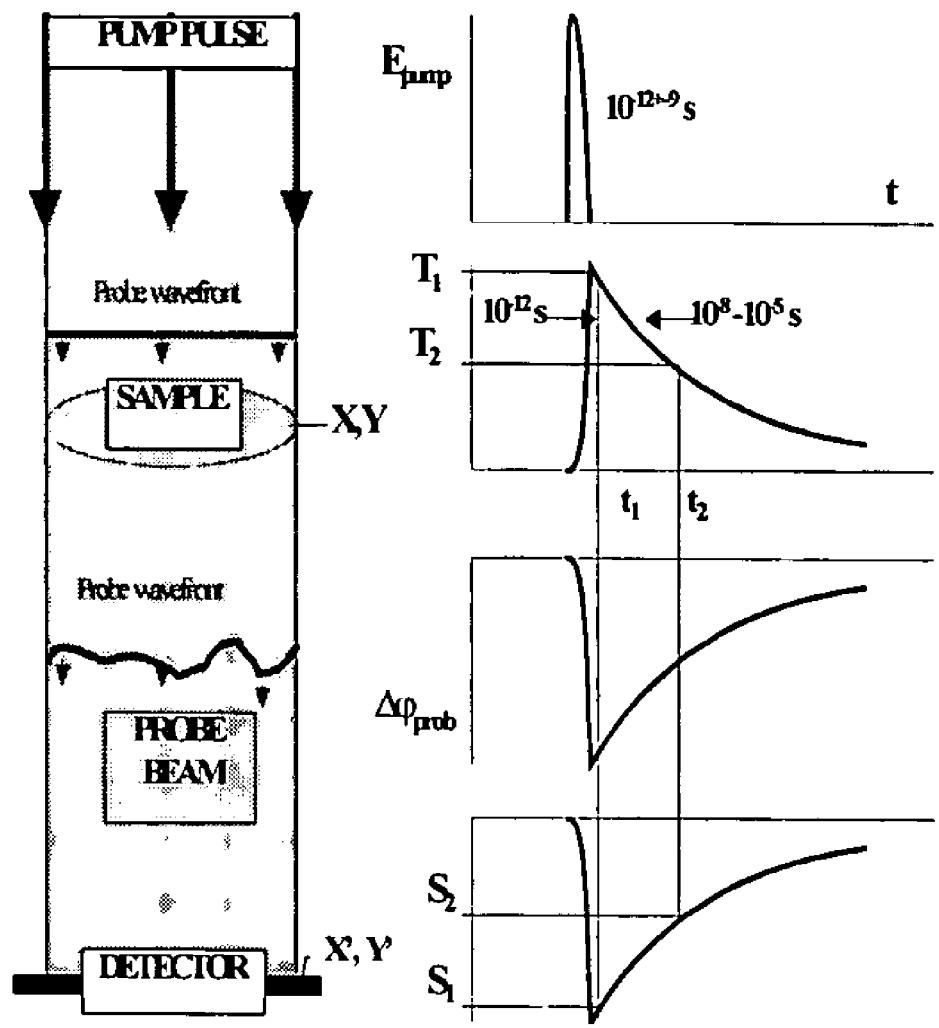
FIG. 1 is a schematic presentation of the method claimed.

The next step of the method is irradiation of the object containing absorbing microheterogeneities by a focused pump laser beam having a short pulse width and a wavelength coinciding with the absorption line of the microheterogeneities observed (FIG. 1a). The pump pulse immediately irradiates a relatively large sample surface, the size of said surface being larger than the wavelength of the pump laser used.

In fact, said surface could be of any size, but logically, it couldn't be larger than the sample itself.

Said effect being in progress, light energy absorption in the sample is not uniform: microheterogeneities absorb light most actively. Thus, a live cell has various absorbing structures (cytochromes, organelles, mitochondria, etc.), the size of said structures varying from a few nm to hundreds of nm, i.e., considerably smaller than the average size of a cell (5–20 mkm). However, their ability to absorb light is so high, that it causes thermal effects leading to the temperature rise 10–1000 times higher than the temperature of the cell's environment. Cooling of the structure (FIG. 1c) that has absorbed light energy begins owing to heat diffusion after the end of the pump pulse operation. The time of cooling for a single sphere-looking object is $$\tau_T = \frac{R^2}{6.75K}, \quad (2)$$

where
$t_T$ is the time of cooling of the object, sec.
R is the radius of the object, m
K is the thermal diffusivity (m²/c).

Said time is $10^{-5}$–$10^{-4}$ sec. for the majority of blood cells.

A primary thermal response could be presented as the distribution of temperatures over the x-axis and the y-axis:

$$\Delta T(x,y) = \alpha(x,y,\lambda)\frac{\varepsilon(x, y)}{\rho C}, \quad (3)$$

where
$\Delta T$ is the distribution of temperatures over the x- and y-axes,
$\alpha$ is the light energy absorption coefficient with the wavelength,
$\rho$ is density, kg/m,
$\varepsilon$ is energy density in the pump beam, J/m²,
C is thermal capacity, J/kg °C.

Expressions (2) and (3) help estimate the temperature effect both for an object (a cell) as a whole and for its structural elements, i.e., absorbing heterogeneities. The intensity of said effect depends on a specific absorption coefficient and the heterogeneity's size. For the submicron structures having the sizes smaller than the wavelength ($10^{-7}$ m), $t_T$ would be about $10^{-8}$ s and less. It means that significant rise of the local temperature could be achieved only providing the pump pulse width or the modulation period T=1/f (where f is a modulation frequency) are smaller or at least comparable with $t_T$. Otherwise the local temperature effect, being the very source of the local heat variations of the refraction index, would not be achieved. Said local heat variations of the refraction index $\Delta n(x, y)$ induced by the pump pulse absorption could be presented as follows:

$$\Delta n(x, y) = \alpha(x, y, \lambda)\frac{\varepsilon(x, y)}{\rho C}\left(\frac{dn}{dT}\right)p, \quad (4)$$

where
$\alpha$ is the light energy absorption coefficient with the wavelength,
$\rho$ is density, kg/m,
$\varepsilon$ is energy density in the pump beam, J/m²,
C is thermal capacity, J/kg °C.
T is temperature A further step to accomplish the method claimed is irradiation of the object containing heated absorbing microheterogeneities by the probe laser beam (shown in FIG. 1 and FIG. 2), the chosen probe beam diameter not being smaller than the pump beam diameter and not being larger than the maximum overall dimensions of the sample. Intensity of the probe beam should be considerably (at least 5–10 times) smaller than the pump beam intensity, so as to cause minimal effect on the measurement results. The phase of the probe beam wave front will be distorted owing to said local heat variations of the refraction index when the probe beam would propagate through the sample. Said phase deviations $\Delta\phi(x, y)$ could be described as follows:

$$\Delta\varphi(x, y) = L\alpha(x, y, \lambda)\frac{2\pi\varepsilon(x, y)}{\lambda_0 \rho C}\left(\frac{dn}{dT}\right)p, \quad (5)$$

where
L is a geometrical length of the probe beam way in a heterogeneity,
n is the refraction index,
$\Delta n$ is the refraction index variations on the x- and y-axes,
$\alpha$ is the light energy absorption coefficient with the wavelength,
$\rho$ is density, kg/m,
$\varepsilon$ is energy density in the pump beam, J/m²,
C is thermal capacity, J/kg °C.
T is temperature.

It is a further step of the method claimed to transform the diffraction limited phase distribution of the probe laser beam over the whole cross-section (FIG. 1d) to an amplitude image using the phase contrast method.

Taking into account the values $\phi_0(x,y)$ and $I_0(x',y')$ previously obtained in an unexcited state, parameters of the probe beam propagated through the exited sample at the moment of time to could be presented as follows:

$$\phi(x, y) = \phi_0(x, y) + \Delta\phi(x, y) \qquad (6),$$

where $\phi_0(x, y)$ is the probe beam phase in the absorbing zone of an unexcited object, $\Delta\phi(x, y)$ is alteration of the probe beam in the absorbing zone of an unexcited object, $$I(x', y') = I_0(x', y') + S(x', y') \qquad (7),$$

where $I_0(x', y')$ is the amplitude of the photothermal signal in an unexcited state, $S(x', y')$ is the required photothermal signal being subject to registration and analysis.

The size of separate microheterogeneities larger than the pump laser wavelength is determined using structural analysis of said amplitude image measured immediately at the moment of the pump laser operation and corresponding to the refraction index change distribution induced by the pump laser in the object observed.

To determine the average size of the microheterogeneities smaller than the wavelength, the phase alteration speed of the diffraction-limited images of said microheterogeneities in various points of the probe beam cross-section should be measured, said measurement beginning immediately after the pump pulse effect has taken place. To achieve this, the probe beam irradiation and the phase distortion analysis of the object are performed a number of times, e.g., at two moments of time (shown in FIG. 1d and FIG. 1e).

Theoretical limit of this method is conditioned by the terminal time of transformation of optical energy to thermal one, said time being $10^{-13}$ sec. for condensed mediums. Said time corresponds to the size 1A and could be achieved using femtosecond lasers. In the method claimed, the PT signal amplitude S is proportional to the temperature change in the absorbing zone and decreases owing to thermal diffusivity.

The most significant feature of the method claimed is that only the value of the PT signal, the moments of time when the signals are measured and the thermal diffusivity value of the medium are needed to determine the size. The preliminary estimation of the optical properties of the sample is not needed anymore. Said measurements are possible on the following conditions: linearity of the PT signals; linearity of the pump pulse absorption processes, the pump pulse width being much smaller than the time of cooling.

Beside determining the sizes of the absorbing microheterogeneities being much smaller than the diffraction limit, one of the fundamental issues is obtaining information about precise location of said microheterogeneities. Conventional microscopes lack such information, and the precision of localisation is determined by the size of the diffraction stain. In the invention claimed precision of the microheterogeneity's location could be much higher due to the possibility of obtaining additional information about the size of microheterogeneities, using measurement of the microzone thermal profile and its conduct in the cause of time. The method described could give information about the heterogeneity's location with the precision right up to 0.05–0.01 of the wavelength. Thus, resolution capacity for two microheterogeneities would not be worth than 25 nm when operating in the visible range of the spectrum with the central wavelength of 500 nm.

The general presentation of the device for implementation of said method is shown in FIG. 3. The device comprises unit 1 of the pump laser (a pulse or continuous one, depending on the measuring method), unit 2 for the probe beam formation, forming optical systems 3 to focus both beams on the object observed, junction 4 to lead the beams into unit 5 of the probe beam optical transformation, the latter unit being an optical system of the phase contrast to transform phase distribution in the probe beam cross-section to an amplitude image. Said unit consists of two parts: focusing optics 5a and converging optics 5b. The device also includes unit 6 of the probe beam registration. Units 3 and 4 could be realized as a standard phase-contrast microscope. The registration unit 6 is realized as a multi-channel photodetector 7 on the basis of a high-speed CCD-camera. Unit 6 allows registering said amplitude image of the probe beam at various moments of time as related to the pump laser pulse moment. Unit 6 also contains a number of one-channel photodetectors 8 to register time amplitude changes for one or several zones in said amplitude image of the probe beam, the probe beam falling simultaneously on all said photodetectors due to unit 9 presenting the image of the probe beam. The unit is realized as a system of semi-transparent mirrors placed on the way of the probe beam behind the phase-contrast system. Another version of unit 9 is a consecutive spatial shift of said photodetectors 8 using an additional switch unit (not shown). A fundamental feature of the apparatus claimed is the presence of unit 10 of synchronization and unit 11 of the regulated time delay, the latter unit being placed between unit 10 and unit 2. Unit 10 is also connected with the control entries of unit 1 of the pump laser, unit 2 of the probe beam formation and unit 6 of registration, as well as with the control exits, namely with those of unit 10 of synchronization and unit 12 of turning. Lasers of any spectral range (e.g. those of UV and IR ranges) can be used as unit 1 of the pump laser depending on the object of examination. In fact, using compact pulse semiconducting lasers with the pulse width up to a few nanoseconds would be highly convenient.

The device operates as follows. Both coaxial-focused laser beams affect object 13, namely the pump laser pulse and the coaxial pulse probe laser beam. A thermal heterogeneity induced by the pump laser and connected with the microheterogeneity examined causes alteration of the probe laser beam parameters. All such alterations within the limit of the probe beam cross-section are registered using photodetector 7. The signal registered by photodetector 8 determines thermal relaxation of the heated microheterogeneity and consequently the size of the microheterogeneity examined. Photodetector 7 serving to register the probe beam image of the microheterogeneity examined allows visualizing separate microheterogeneities, their size possibly being smaller than the diffraction limit on resolution, which makes examination using a regular optical method impossible. However, thermal image appearing when heating by the pump laser pulse 1 is, as a rule, significantly larger than the microheterogeneity itself due to the heat diffusion effects. Said thermal effect allows determining the image structure and the size of the microheterogeneity observed, as its refraction index differs from the refraction index of the surrounding medium.

The invention claimed is illustrated, but is not limited by the following examples.

EXAMPLE 1

Study Microsamples in Diffraction Limited Image Mode

Figure 5:
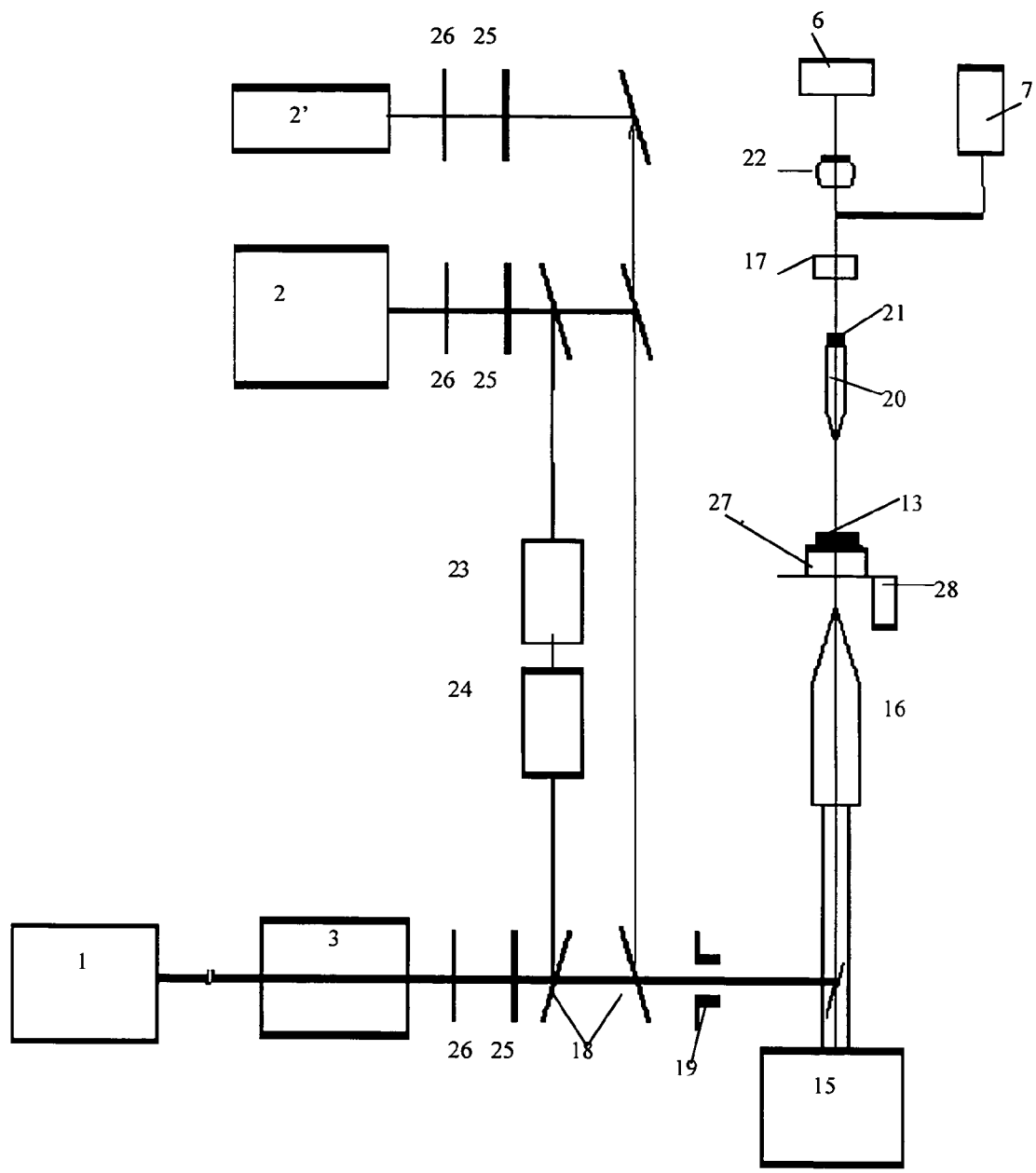
FIG. 5 is a scheme of the apparatus using an additional continuous probe laser and a registration device wherein the second photodetector comprises one or several photoelements.
Figure 6:
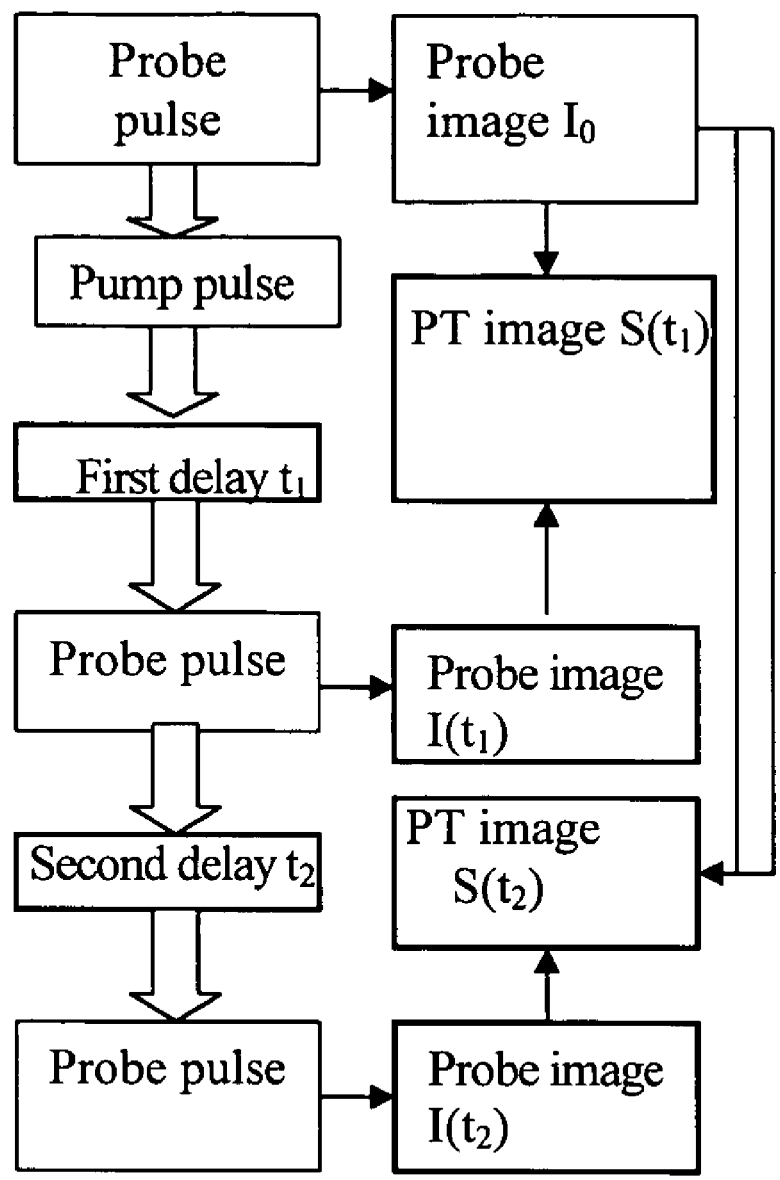
FIG. 6 is an algorithm for obtaining photothermal image with a time resolution and for determining the sizes of absorbing microheterogeneities in the object.

Technical basis for implementation of the device (shown in FIG. 5) is a standard optical microscope 15, equipped with unit 1 of the pump laser and unit 2 of the probe laser, photodetectors 7 and 8 and an apparatus-program device (not shown) to control the device components. The pulse pump laser of unit 1 allows irradiating the object in the visible diapason of the wavelengths ranging from 400 to 600 nm (parametrical solid state laser with the pump Nd: YAG). The pump beam is transformed to a one-mode beam using a forming unit 3 made as a spatial filter, and is focused on object 13 through an entry device 4 and a standard condenser of microscope 16. The pump irradiation is blocked by filter 17 after the object has been propagated. A probe laser 2 is a dye pulse laser having the duration of 6 ns and the wavelength of 630 nm and the energy regulated in the range of 1–100 nJ and focused (as an analogue to the pump beam) on the stain with the diameter of 10–20 μm in the surface of object 13. The pump and the probe laser beams are combined on mirror 18 and after that go coaxially. The probe beam diameter in the surface of the object is larger than the size of said object. It provides for the momentary visualization and diagnostics of the samples with the diameter smaller than 15 μm with the spatial resolution about 1 mkm depending on the microscope used. The advantage of the scheme used is that the image obtained is not dependent on the location of both laser beams as related to each other and to the object, as the source of the signal is not the pump beam itself, but local absorbing zones with the size considerably smaller than the size of both laser beams. Most biological samples have said sizes on cellular and subcellular levels. The probe laser lighting and its registration are realized using the phase contrast method. To implement this, the device claimed utilizes diaphragm 19, condenser 16, micro lens 20 (20×0.4), quarter-wave mask 21 and lens 22, diaphragm 19 and mask 21 being optically conjugating elements. Spatial distribution of the probe beam phase gradient in the surface of the object is transformed to the probe beam intensity distribution in the surface of the image (registration unit 6) using the scheme described. Thus visualization of the phase distribution could be achieved. The device operates using the following algorithm. The image in the probe beam $I_0$ of an unexcited object (before it has been irradiated with the pump pulse) and another image in the probe beam at the moment of time t (after irradiation with the pump pulse is over) are registered. The image being the difference of the two images obtained is called photothermal image.

$$S(x,y,t,\lambda) = k_1/E_{pump}(\lambda)[I(x,y,t)k_2/E^t_{probe} - I(x,y,0)k_2/E^0_{probe}] \quad (8),$$

where $S(x,y,t,\lambda)$ is the required photothermal image, $k_1$ and $k_2$ are gauge constants of the energy sensing elements 23 and 24, $E_{pump}$ is the pump pulse energy, $E^t_{probe}$ and $E^0_{probe}$ are energies of the two probe pulses, $I(x,y,0)$ is the pfotothermal signal amplitude in an unexcited state $I(x,y,t)$ is the pfotothermal signal amplitude at the moment of time t after irradiation with the pump pulse is over.

Figure 7:
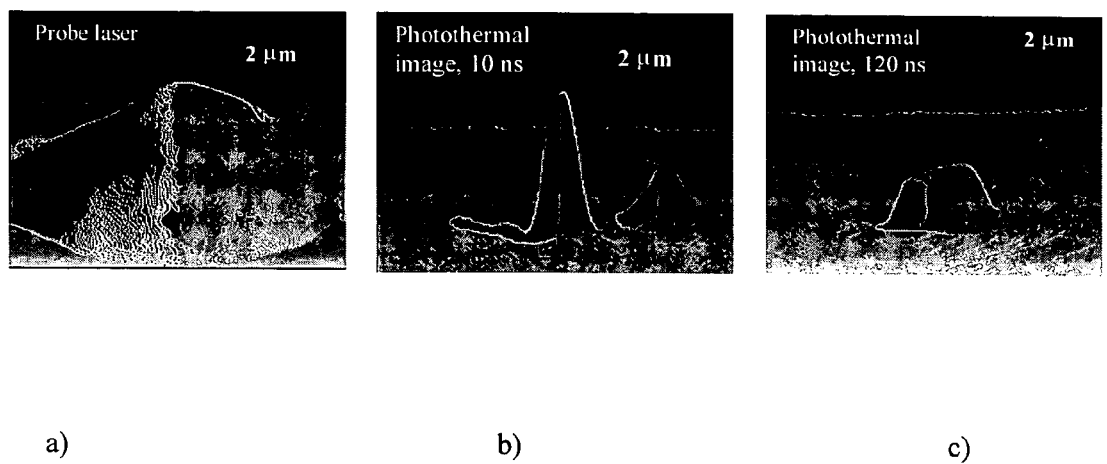
FIG. 7 is an example of a photothermal image of a single heterogeneity with the dimensions of 200 nm.

Expression (8) allows using images of the probe laser beam to calculate PT image even if they are registered at unequal levels of the probe pulse. Delay between the pump pulse and the probe pulse is achieved using fiber spatial filters in the range from 10 to 200 ns. It corresponds to the cooling time values of the microheterogeneities with the sizes from 50 nm to 1 μm. Registration of the probe beam image is performed in the real time by the CCD-camera, two modes of registration of the photothermal image being possible. The first mode is as follows: probe pulse—pump pulse—delay 1—probe pulse—delay 2—probe pulse. The photothermal images obtained using said mode are shown in FIGS. 7a–7b.

In case the cooling time values and the delay values are very small and the camera cannot register posterior images of the probe beam, a strobe mode is possible: probe pulse—pump pulse—delay 1—probe pulse—pause to check the image—delay 1+2—probe pulse. The difference between the two modes is as follows: the sample is irradiated by the pump pulse more than once in the strobe mode, the number of said operations depending on the number of the PT images registered. The pump pulse width (8 ns), the probe pulse width (6 ns) and the time delay (from 10 ns) determine spatial resolution of the method. This allows estimating absorption size and coefficient in separate zones having the size up to 50 nm. Absorption sensitivity of the PT microscope described is determined by the dynamic range of the image-detector (14 bit) and allow registering alteration of the probe beam amplitude image with the precision up to 0.1 percent. The sizes of the photosensitive elements allow achieving the image quality on the level of 10 pixel/μm. According to the algorithms described, the computer (not shown) uses system of shutters 25 to control the generation sequence of laser pulses.

Figure 8:
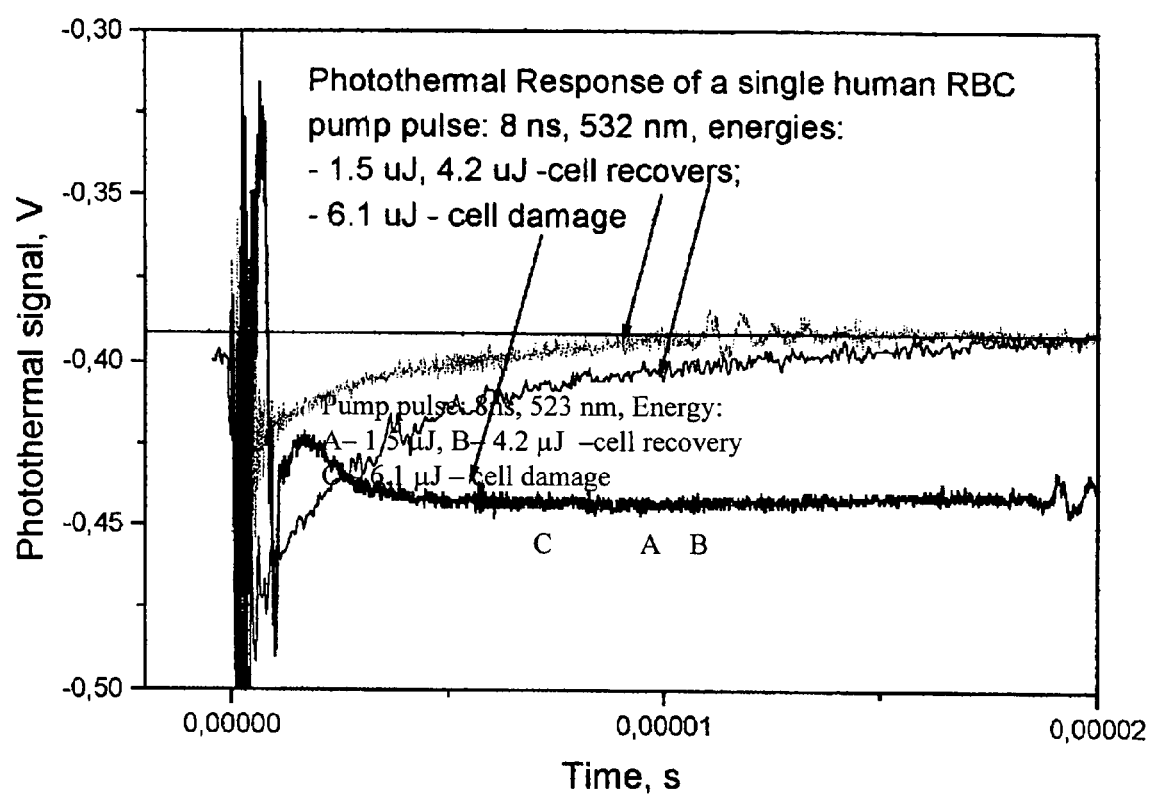
FIG. 8 is a time diagram of the photothermal response of a single human erythrocyte by various pump beam intensities.

According to another version, the PT microscope utilizes continuous probe laser 2 to register the sample time response to the pump pulse. A time diagram of the photothermal response of a single human erythrocyte by various pump pulse intensities is presented in FIG. 8. Time dependence of the probe laser amplitude is registered as follows: 1) in a chosen point or part of the image; 2) an integral one, over the whole surface of the object.

The wavelength and the probe laser beam parameters are analogous to the pulse probe laser. The continuous laser intensity is minimal, so as, on the one hand, to allow registering the signal by photodetector 7 and, on the other hand, to provide conditions for the unexciting cell diagnostics. Photodetector 7 of the diode type with time resolution of a nanosecond range is used. The measurement mode described could be applied with the registration of photothermal images, simultaneously or separately. It provides for PT microscopy of submicron absorbing microheterogeneities.

Figure 9:
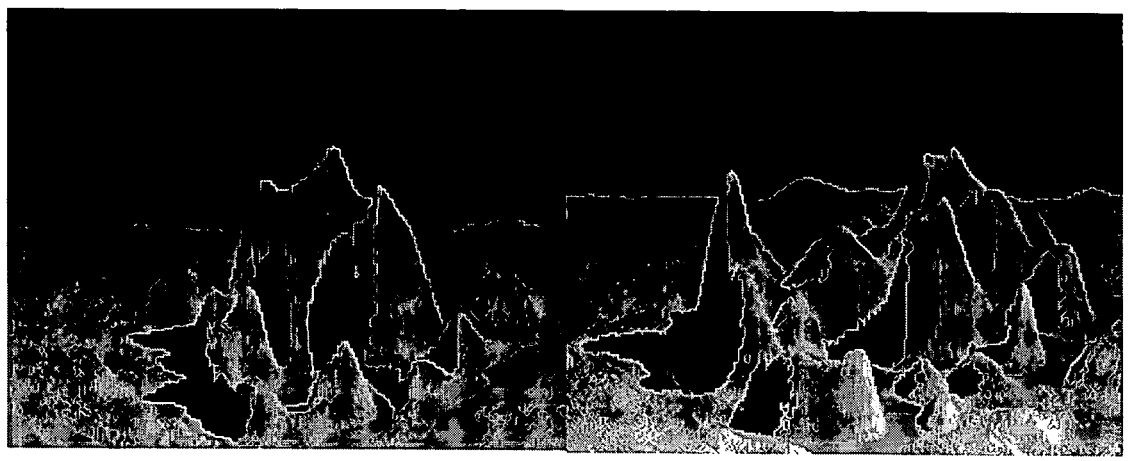
FIG. 9 is an example of a photothermal image of a neutrophil in two different structural-functional states.

Requirements to the pump pulse are to obtain a distinct PT signal in the linear mode and to exclude damage of the sample. For example, the photothermal image (FIG. 9) for uncolored live human neutrophil is provided by the pump pulse energy 10–40 μJ and regulated by filter 26, providing the pump wavelength is 532 nm and the beam diameter is 12 μm. Higher levels of the pump energy are used to determine cell resistivity to the laser pulse and attendant thermal and mechanical load. The pump pulse width of 8 ns is a compromise between the necessity of sufficient time and spatial resolution to diagnose submicron zones having the sizes up to 50 nm, and the light intensity low enough to exclude optical damage of the cells.

To examine live cells, micro sample chamber 27 and an automatic scanning stage 28 are used, the latter being utilized by the computer to position each cell observed on the place corresponding to the laser beam center. Each sample chamber 27 contains 0.5 µl of the cell suspension having the optimal concentration of $10^6$ and $10^6$ cells/ml. The scanning stage provides for the positioning of a number of sample chambers. It allows examining separate cells and their populations in the real time mode. The micro sample chambers used provide for the safer and more stable conditions for live cells as compared to the slide/cover glasses used in microscopy.

It is sufficient to measure said energies to increase the precision, providing a spatial profile of the laser beams is stable. Using lasers with an unstable spatial profile could cause the need in additional CCD-cameras to control said profile from impulse to impulse independently.

EXAMPLE 2

Implementation of a Laser Photothermal Microscope to Examine Biological Micro-Objects 2.1 Active diagnostics. When examining biological objects of a single cell type, the definition of active diagnostics in the method claimed is significantly widened and even partly altered. The reason is that it assumes not only examination of the value of thermal effects induced by radiation, but also examination of the cells' reaction to the dynamic (short-time) thermal excitement. It is important for many applications, and more particularly for the objects of laser medicine, laser safety and examination of the fundamental cell properties, examination of external effects including radiation, etc. The method for examination in this case is examining and comparing cells' reactions to various energies of the laser pump. Said reactions could be examined using both independent methods, e.g. biochemical and histological, and the pofotothermal method itself. The measurement scheme and the laser parameters described in example 1 could be used as an example. The difference is analysis of the photothermal signal amplitude conduct (the photodetector signal corresponding to one point on the probe beam phase image) and analysis of its shape with the pump laser energy gradually increasing in the range of $10^{-6}$–$10^{-3}$ J.

The analytical method depends on the range of dynamic temperatures in a cell, the temperatures being induced by the pump laser. Thermal activation of metabolic processes, inactivation of ferments and local modification of a membrane structure, are basic effects in the range of "safe" temperatures (approximately up to 60–70° C.). The character of said processes depends on the character of the time-spatial distribution of the temperature field. For, example, the temperature field profile can in the first approach be volume-homogeneous because of the relatively homogeneous spatial distribution character of absorbing molecules when choosing a wavelength in a protein and DNA absorption zone in the ultra-violet zone or in the water absorption zone in the infrared zone. And a quite different situation appears when operating in a visible spectral range, wherein the high sensitivity of the method claimed allows examining low absorption undetectable by the methods already existing. Besides, the present method for examination of absorbing microheterogeneities and their sizes by super-short pump laser pulses (about $10^{-9}$ sec and less) allows examining a cell's response to the local heating because of the absorption on separate endogenous chromophores with the size varying from 10 to 1000 A. It should be noted that localization of heating is achieved providing the sizes of said microheterogeneities are small and the pulse width is shorter than the time of cooling of the local heterogeneities. Otherwise local heating spread over the whole cell because of the heat diffusion, and the cell's response character could also vary from a local to an integral one. The cell's response could be determined using a biochemical probe technique, an electronic transmission microscope or an electronic-spin resonance technique (ESP). Said effects could cause change of intra-cell physiological processes, the processes of respiration and energy generation being the most sensitive to heating. In case the reaction is remoter, it is examined by continuous monitoring of the phase conduct of the continuous probe beam, or using the mode of the pulse beam or probe beam repetition (in this case less pump laser energy is used). Said energy allows eliminating heat effect perceptible by the cell and is used to perform only non-invasive diagnostics of the chromophores-indicators state by the change of their absorption (concentration), sizes and location in a membrane structure.

The pump laser energy increased to the range of 70–90° C. could cause cell damage due to conformation processes and heat denaturing of proteins, e.g., in a membrane structure. As a rule, the change of their optical properties, increased density or changes of thermal properties attend it. E.g., transparency of cytoplasm proteins decreases, and v.v.: denaturing of collagen structures causes the reverse process. Proteins or other structures could compress and dissociate to separate fragments. According to the expression for the photothermal image, said effects would cause alteration of the photothermal signal parameters in this or that way.

Possible role of the heat attending effects should be mentioned, including the effect produced by mechanical and acoustic factors on membrane structures.

2.2 Photothermal examination of the life time of the optically induced physical-chemical processes. When using pulse excitement, the PT signal form is determined by a relatively fast exponential growth of its front with the characteristic time $\tau_\Sigma$ and a relatively slow exponential fall determined by the time $\tau_T$ (2). Resulting relaxation time depends on the relation of the following relaxations: non-radiation relaxation $\tau_{NR}$, radiation relaxation $\tau_R$ and the rate of photochemical reactions $k_{PH}^{-1}$ $$\tau_\Sigma = (\tau_{NR}^{-1} + \tau_R^{-1} + k_{PH})^{-1}, \qquad (9)$$

Thus, the PT method allows determining time of a dominating relaxation (said time being different for different absorbing structures), providing a super-short laser pulse has the width $t_p < \tau_\Sigma$ and a photo-registering system is high-speed enough. For example, the PT method allows determining the time $\tau_{NR}$ being in the range of $10^{-11}$–$10^{-13}$ sec by $\tau_{NR} < \tau_R$, $k_{PH}^{-1}$. The difference of the method claimed from the existing methods for determining quantum yield of photochemical processes or intra-molecular transformations of the energy absorbed is as follows. According to the method claimed, said quantum yield could be determined both on the level of single cells and on the level of separate intra-cellular absorbing structures. The time of signal decay, said signal being determined by the value $\tau_T$, could be measured using expression 2, so as to obtain additional information about the sizes of microheterogeneity. Said method allows examining the overlapping microheterogeneities, providing the sizes of said microheterogeneities are larger than the diffraction limit. For example, the PT signals from two microheterogeneities would be registered simultaneously at the short time delay $\tau_{del}$ between the pump pulse and the probe pulse $\tau_{del} < \tau_T^1$, $\tau_T^2$, where $\tau_T^1$ and $\tau_T^2$ are the times of cooling of the microheterogeneities with the radiuses $R_1$ and $R_2$ ($R_1 < R_2$, $\tau_T^1 < \tau_T^2$ correspondingly), while at the longer delay $\tau_T^1 < \tau_{def} \tau_T^2$ mostly PT signals from a larger microheterogeneity would be registered. Comparing two or more images, taking into account their thermal blurring due to the heat diffusion, allows obtaining information about absorption of a smaller microheterogeneity overlapped by a larger one. Information about the sizes of microheterogeneities less than the diffraction limit could be obtained on the basis of dynamics analysis of the diffraction spot intensity decay, and more particularly, on the basis of determining zones with various slope of said dependence corresponding to various times of cooling of the microheterogeneities with different sizes. Analogous information about the relaxation time values could be obtained in the intensity modulation mode of the pump laser on the basis of analysis of the probe beam time phase, using existing methods developed to measure the time of oscillatory relaxation in gases.

2.3 Intra-cellular dynamics study. Numerous structures within a cell, and separate organelles in particular, can be in constant movement (vibration, rotation, onward movement). Thus the onward movement speed can be as high as 1–3 μm/sec. As many organelles contain radiation-absorbing chromophores, e.g., cytochromes, analysis of the organelle movement could be performed by obtaining the photothermal images at various moments of time consecutively, e.g., with a 1–2 sec delay. Further comparison of said images including analysis of spatial location of separate peaks in the structure of said images should be performed.

2.4 Analysis of the external conditions impact. Impact of various factors (radiation, temperature, drug, etc.) can cause the change of properties of absorbing chromophores through the series of dependent biochemical processes. This in turn would cause the corresponding parameter change of the photothermal signals. According to expressions (2)–(9), the impact of external factors, e.g., radiation, can appear as the change of concentration or absorption of chromophores, as well as the change of relaxation times, sizes of chromophores, etc. More particularly, clusters of mitochondria as big as a few μm dissociate to separate structures as big as hundreds of nm, the latter continuing then slowly collapsing. Thus, the size monitoring of the absorbing structures using the methods suggested by changing the parameter $\tau_T$ (2), allows examining various impacts from stimulation to inhibition right up to the display of toxic effects in a cell. 10 percent of the energy absorbed would be transformed to heat for the values $\tau_R$ and $\tau_{NP}$ $10^{-12}$ sec and $10^{-11}$ sec respectively. External impacts can influence both bleaching of fluorescence and its increase. It can cause a significant change of the photothermal signal amplitude, up to several order. Analogous effect can also appear, providing external factors affect the change of the $k_{PH}$ parameter.

2.5 The use of photothermal probes. The area of potential applications of the photothermal method widen significantly, providing artificial absorbing (colored) microheterogeneities are placed in various biological structures, and first of all, inside the cells. For example, said microheterogeneities could be micro-spheres made of various materials and performing the role of photothermal (PT) probes. The pump radiation could both be used to directly visualize them using dozed heating, and to simultaneously implement this or that method for selective impact on biological structures. More particularly, small golden metal sphere with the sizes ranging from a few nm to hundreds of nm, non-metal fragments (polystyrene, etc.), various micro-capsules to drug deliver liposomes with various fillings, and photo-sensitizers used in the method for photodynamic cancer therapy, etc., could be used as PT probes. Type of application of the present method depends on the PT probe purpose. In case PT probes are accumulated in pathological zones, e.g., oncologic cells, or bacteria, selective affection of such objects due to irradiation by a wide laser beam is possible. Said beam would selectively heat and, consequently, thermally killing only the cells containing said PT probes. The method claimed could visualize the location of such probes, as well as estimate their heating necessary to thermal killing the cells. In case small metal spheres with the sizes ranging from a few nm to hundreds of nm are used, they are visualized due to the heating of the environment that is transparent for the probe radiation. Another example is determination of the drug carrier location inside the cell, as well as visualization of the drug yield process from the carriers under the influence of various factors (dissolution of the walls, their chemical and thermal destruction, the use of external laser radiation, etc.). It should be mentioned that the present method could use the existing probes, those used in the fluorescent diagnostics in particular. It can be explained by the fact that not all absorbed radiation from the excitation source is transformed to the secondary fluorescent radiation, as a rule. The rest of it is transformed to heat because of non-radiation transitions. More particularly, $\eta_T \sim 1$ would correspondingly be obtained from (9) for the typical values $\tau_R$ and $\tau_{NR}$ $10^{-9}$ and $10^{-11}$ sec. Thus, the major part of the energy absorbed is transformed to heat even in the existing fluorescence probes, while only 1 percent is transformed to fluorescence. The main problem is yet obtaining a good contrast. The fluorescence method achieves this by the lack of fluorescence in the probe's environment. As for the PT method, a good contrast is expected to be in the visible spectral zone where the cell absorption is relatively small: about $10^{-2}$–$10^{-3}$ cm$^{-1}$, while the probe absorption could achieve $10^0$–$10^2$ cm$^{-1}$, i.e., the expected contrast is $10^2$–$10^5$. It shows the fundamental opportunity to combine the PT method and the PT probes with a well-developed fluorescent probe technique for selective analysis of various cellular structures, including combinations with the fluorescence method. Calibration of the PT method sensitivity both on absorption and on temperature could be performed by using the introduction of PT probes in the cells, said probes having specific sizes and an absorption coefficient, e.g., due to filling the liposomes with standard solutions.

2.6 Analysis of absorption in thin films. Another possible application of the invention claimed is examination of surfaces of different types ranging from metal ones to the surfaces of transparent dielectrics with various covers. The examples worth mentioning are as follows: identification of fingerprints, PT photometry of photographic plates (PT densometry) and films, etc. Application of the PT method to analyze distribution of already non-fluorescent biological molecules on the surface of various micro-matrixes, microchips, including analysis of gene expression in toxicology, is especially promising as an analogue to the fluorescence method. The pump laser irradiation illuminates the surface of the under-cover with a corresponding coverage, and more particularly with a layer of molecules on the glass, that are heated by said irradiation due to absorption. The temperature of heating is insignificant, about several degrees ° C. Appearing gradients of the refraction index are then registered using the probe beam (see example 1). The pump beam diameter, as well as the probe beam diameter could be large enough, and as large as tens and even hundreds of micrometers. A laser on dyes is advisable to be used here as a source of the pump radiation, said laser being restructured according to the wavelength using a set of dyes in a wide zone of 200 nm to a few μm. Absorption in DNA can also be registered in an ultra-violet zone of 200–280 nm.

The thickness of the film or the layer of molecules could be determined by their times of cooling, providing the under-cover is transparent and absorption is relatively homogeneous within the structure analyzed.

2.7. Other Biological Applications.

2.7.1. Examination of the PT images of cancer cells with focus on the analysis of microstructures according to said methods. Comparison of said images with the images of normal cells would allow developing criteria for early diagnostics of cancer diseases.

2.7.2. PT microscopy of the multi-photon absorption achieved by using focused radiation of picosecond and femtosecond lasers. Such method would not only allow examining fundamental optical properties of biomolecules, but also significantly increase longitudinal spatial resolution due to the probe beam registration of, as a rule, thermal excitements in the pump beam caustic zone. It should be mentioned that the usual scheme of the thermal lens in the mode of consecutive scanning of both beams could also be used in such a microscope because the zone of photo-damage is small.

2.7.3. Obtaining the PT images in the super-resolution mode of separate small bio-objects of a DNA element type, separate chromosomes, melanosomas with single granules of melanin, etc. Examination of melanosomas is particularly important as related to the photo-dermatology issues and cosmetology dealing with the pigment stain treatment, hair removing, determination of eye-safe dozes, etc.

2.7.4 Combination of the PT method and the other methods. As it has already been mentioned, combination of the PT method and the methods supplementing it is highly promising. This concerns both the fluorescence method and the optical-acoustic and PT radio-metric methods. Said methods can use (with slight modifications) all the micro-heterogeneity analysis methods claimed, including estimation of the micro heterogeneities' sizes, as the mechanisms of forming yield signals in the former methods are analogous. The PT method could be combined with usual optical tweezers to fix the cells, elements of the same microscope being possibly used to perform this. The combination technique is also highly promising for examination of quanta-mechanical effects, black micro-vacancies (dots), etc.

EXAMPLE 3

The Mode for Photothermal Measurement of Submicron Microheterogeneities

One of the issues of intensively developing nanotechnologies in various scientific and technical fields is the lack of precise control of the technological processes forming new structures with the resolution capacity as large as a few run. The method claimed allows solving the problem using high resolution provided by the change of the nanostructures' cooling speed using the sources of laser radiation. An example for practical realization: the pump laser unit: a femtosecond pulse laser Cr:LiSAF, wavelengths, 850 nm in particular, energy range 1 µJ–3 mJ, pulse width $10^{-13}$ sec., the delay unit being realized as an optical delay line, a part of the pump beam being used as a probe beam. The expected resolution is 1–5 nm. Beside visualization of nanostructures, the device claimed also provides for the accomplishing of the control function and the impact function due to the strong interaction with sample because of the high dynamic parameters. Said parameters are as follows: the value of the local temperature gradient could be as high as hundreds and even thousands degrees, and the gradient of the pressure value could be as high as tens of thousands of atmospheres. Thus, the structure of materials could be modified in any given point and by any given method due to the introduction of artificial absorbing microheterogeneities by various impregnation methods, said microheterogeneities being controlled independently using the electronic microscopy methods.

Modification could be performed owing to the inducing structural chemical processes, including additional affection by radiation and ultra-sound. As concerns biology, the present method could be used to modify membrane structures on the surface of the cells and in various intra-structures, as well as to modify the DNA structures in the required chain zones with the simultaneous control of this process using the device claimed. For example, parts of a DNA chain with various anomalies could be eliminated using said method, and vice versa, they could be modified as required. Another example that has already been partly mentioned deals with the control of selective delivery of drug to any point of a cell using liposomes (cell therapy) and the visualization of location of said liposomes within a cell. A more powerful pump laser pulse combined with ultra-sound could be used to selectively destroy membranes of liposomes, so as to release contained drug in a required zone under the control of the method claimed.

EXAMPLE 4

Photothermal Method for the Examination of Absorbing Microheterogeneities in Solid Optically Transparent Materials The problem is topical for the optics producing technology and the technologies of producing active mediums for powerful lasers, super-pure materials for optical connecting lines and super-pure semi-conductors for electronic industry. Pulse lasers with the wavelengths within the optical transparence zone of the materials observed, but coinciding with the absorption line of possible heterogeneities having different natures (physical, chemical, etc.), are used as the pump lasers. The wavelengths are ranged from the ultra-violet (180 nm) to infrared (10.6 µm) diapasons and higher. Examples of the lasers used are as follows: eximer lasers, dye lasers, the first and additional harmonics of a neodymium laser, holmium lasers 2.1 µm, erbium lasers, $CO_2$ (10.6 µm). Spectral range of such a laser is chosen within the transparence zone of the materials observed and within sensitivity of the detectors used. In the majority of cases the lasers of the visible and near infrared range satisfy said criteria, and high-speed CCD cameras could be used as photodetectors.

Example of implementation: pump laser—third harmonica of YAG:Nd laser, wavelength 355 nm, pulse width 3 ns, pulse energy up to 1 mJ, diameter of the focused stain about 30 nm, probe laser—semi-conducting continuous laser with the wavelength of 780 nm. KDP ($KH_2PO_4$) and DKDP ($D_xH1-x02\ PO_4$) crystals are type of the material examined. The size of absorbing microheterogeneities is about tens of nm and the absorption value is about $10^3$–$10^4$ times bigger than the average volume absorption in a crystal. Thus, only the method claimed could solve the urgent problem of visualizing microheterogeneities with said parameters, providing said pulse width according to the presented calculations is observed. Said method also allows examining destruction processes in optical materials affected by pulse lasers beginning from the earliest stages of damage and various mechanisms of said damage ranged from absorption on local impurities to multi-photon effects or an optical rupture.

The present method could use various modifications of the phase contrast scheme (with Fourier's transformation, etc.), as well as other methods for estimating the refraction index change induced by the pump laser, including a heterodyne method, the method of differential contrast interference microscopy, etc. The invention could utilize various laser types as pump lasers: ultra-violet lasers (nitrogen and excimer ones, etc.), dye lasers, solid state lasers (ruby lasers, the first and the second harmonics of a neodymium laser, holmium lasers, erbium lasers, etc.).

In general, the present method for estimating the average size of absorbing submicron microheterigeneities could be implemented with slight modifications using various schemes of photo-calorimetric spectroscopy/microscopy. Said methods are as follows: the lens method for the probe beam defocusing, optical-acoustical method for the acoustical pulse width estimation, deflection methods of the various spatial geometry types, etc. The probe laser wavelength could be chosen depending on the object examined. For example, the wavelength is chosen within the minimal absorption zone of a cell when operating in the linear mode, so as to eliminate possible impact of the probe laser absorption on the results of measurements. An don contrary, the probe laser wavelength is to be chosen within the protein absorption zone, i.e., in the ultra-violet zone, or within a thermal disintegration zone of their products, when examining non-linear effects (and cell denaturing caused by the pump radiation in particular). In the latter case the probe beam phase would carry information mostly about the pump beam absorption, while alteration of the probe beam intensity would carry information about the change of protein absorption or absorption of the protein disintegration products both while the pump pulse is operating and after said operation is over. Introduction of the third beam is possible in the required spectral range to divide the function. Said additional radiation could be both pulse and continuous, from a usual source of the entire spectrum. The analysis of its change, added to the pump wavelength change, would increase identification precision of the components participating in the absorption.

BIBLIOGRAPHY:

1. V. P. Zharov, V. S. Letokhov. Laser Optoacoustic Spectroscopy.—Moscow.: "Nauka".—1984.
2. U.S. Pat. No. 5,781,294 published in 1998 (prototype).
3. V. S. Letokhov. Effects of Transient Local Heating of Spatially and Spectrally Heterogeneous Biotissue by Short Laser Pulses.—"II Nuovo Cimento", v. 13, No. 7.—1991.—pp. 939–948 (prototype).

We claim:

1. A method for photothermal examination of absorbing microheterogeneities in a sample by various external conditions, comprising:
    irradiating the sample observed by a focused pump laser beam and the wavelength coinciding with the absorption bands of the microheterogeneities examined,
    registering thermal effects and accompanied phenomena induced by the pump beam as a result of absorption in the sample, said phenomena including acoustic oscillations, secondary infrared radiation or thermal variations of the refraction index registered by measuring the parameters of the probe beam propagated through the same sample,
    the sample with the surface larger than the wavelength of the pump laser used is irradiated, said surface being of any required size, but not larger than the sample itself; the chosen probe beam diameter not being smaller than the pump beam diameter and not being larger than the sample, and spatial distribution of absorbing microheterogeneities in the irradiation volume being determined by simultaneous estimation of diffraction-limited phase distribution over the whole cross-section of the probe laser beam, said distribution being then transformed to an amplitude image using a phase contrast method;
    determining the size of single microheterogeneities larger than the pump laser wavelength is performed using analysis of spatial structure of said amplitude image;
    determining the average size of the microheterogeneities smaller than the wavelength is performed indirectly, by the characteristic time of cooling connected with said size, on the basis of the dynamics change analysis of the diffraction-limited amplitude images of said microheterogeneities by registering said microheterogeneities either at various moments of time beginning immediately after the pump irradiation is over, the chosen duration of said irradiation not being longer than the characteristic time of cooling of the microheterogeneity observed, or by registering the time phase of the probe beam as related to the intensity-modulated time phase of the pump beam.

2. The method of claim 1 wherein the probe beam is part of the pump laser beam, the delay value being regulated as related to the main beam by propagating said probe beam through an additional optical delay line, the chosen intensity value being considerably smaller, but not less than 5 times smaller, than intensity of the main beam; the size of microheterogeneities is determined by comparing probe beam phases in separate points, said phases being measured by various time delays.

3. The method of claim 1 wherein pulse radiation of the second independent laser with the regulated time delay as related to the pump laser pulse is used as a probe laser beam.

4. The method of claim 1 wherein continuous radiation of the second laser is used as a probe beam, phase distribution being registered in the function of time delay since the pump pulse operation has commenced.

5. The method of claim 1 wherein information about distribution of microheterogeneities over the whole sample surface, the sizes of said surface exceeding the pump beam diameter, is obtained by consecutive estimation of said amplitude image in various sample zones, the distance between said zones being equal to the pump beam diameter, and the transition from one zone to another being performed using a relative shift of the sample and both said beams.

6. The method of claim 1 wherein the pump beam coaxial geometry and the probe beam coaxial geometry are formed when irradiating the sample observed.

7. The method of claim 1 wherein the degree of impact of external conditions on the sample, said conditions being physical and/or drug and/or biological factors, is determined according to the deflection value of spatial-time phase distribution of the probe beam in the process and after the external effect is over, as compared to the initial distribution immediately before the external effect begins, additional information about said effect being obtained using analysis of the optical properties of microheterogeneities with the size smaller than the pump laser wavelength.

8. The method of claim 1 wherein dynamic images of said microheterogeneities induced by the pump beam are obtained by estimation at least two phase images, one of them being estimated immediately before the pump pulse operation and the others being estimated simultaneously with the pump pulse operation or with a delay, with their further subtraction.

9. The method of claim 1 wherein the average size of absorbing microheterogeneities is determined in the pulse mode by estimating the probe beam phase at the place where the microheterogeneity is localized at the two moments of time $t_1$ and $t_2$ after the effect of the pump pulse is over, the average radius of the microheterogeneity being then calculated according to the following formula:

$t_1$ and $t_2$ are the moments of time $S_1$ and $S_2$ are the amplitude values of the photothermal signal at the moments of time $t_1$ and $t_2$ K is the thermal diffusivity of the microheterogeneity's environment.

10. The method of claim 1 wherein the average R size of the absorbing microheterogeneities is determined by estimation of the probe beam time phase as related to the intensity-modulated pump beam time phase $\psi$ from the following formula:

tan $\psi = \omega \tau_T$, where $\omega$ is a circle frequency of the pump laser modulation ($\omega = 2\pi f$), $\tau_T$ is the time of cooling, $$\tau_T = \frac{R^2}{6.75K},$$

K is the thermal diffusivity of the microheterogeneity's environment.

11. The method of claim 1 wherein intensity of secondary infrared radiation from the irradiation zone is additionally measured and transformed to a pulse electric signal, the size of the microheterogeneity being judged by said signal.

12. The method of claim 11 wherein the size of the absorbing microheterogeneity is judged by the speed of said pulse signal decay, the pump laser operating in the pulse mode.

13. The method of claim 11 wherein the size of the absorbing microheterogeneity is judged by the change of said pulse signal phase.

14. The method of claim 1 wherein the amplitude and form of the secondary acoustic signal from the irradiation zone are additionally measured immediately and/or after the form of the photothermal signal has been changed, the acoustic signal being imposed on the photothermal one, and the size of the microheterogeneity being judged by the pulse width of the acoustic signal.

15. The method of claim 1 wherein the samples observed, including cells, are additionally filled with microheterogeneities, e.g., metal spheres, and more particularly golden, plastic uncolored and colored spheres, drug-carriers, e.g., liposomes, magnetic elements, fluorescent probes; the photothermal image of said microheterogeneities being used to determine their location, state and local temperature caused by the pump radiation heating, the sizes of said microheterogeneities being chosen in the range of 1 nm–10 µm.

16. The method of claim 1 wherein information about the spectral properties of separate microheterogeneities is obtained simultaneously with information about the sizes of said microheterogeneities, using estimation of said probe beam phase distribution in the function of the pump laser wavelength, and by at least two time delays as related to the pump laser pulse at each wavelength of the tatter.

17. The method of claim 1 wherein information about longitudinal distribution of microheterogeneities along the pump beam is obtained by consecutive estimation of the probe beam phase distribution by different mutual orientation of locations of the probe laser beam and the object observed, said orientation being achieved by a relative turn of the sample and the probe laser beam with the consecutive reconstruction of longitudinal distribution using Radon's theorem and calculating methods of tomography.

18. An apparatus for photothermal examination of absorbing microheterogeneities in a sample by various external conditions, comprising:

a pump laser pulse unit, a probe beam forming unit, optical forming systems for focusing both beams on the sample observed, a unit for optical transformation of the probe beam behind the sample, and a probe beam registration unit, wherein the unit for optical transformation of the probe beam behind the sample is a phase-contrast optical system to transform phase distribution in the probe beam cross-section to an amplitude image, the registration unit is a high-speed multi-channel photodetector registering said amplitude image of the probe beam either at different moments of time as related to pulse radiation of the pump laser, or at different phases when using modulated continuous pump radiation and/or a number of one-channel photodetectors to register time changes of said amplitude for one or several zones in said probe beam amplitude image, the apparatus being additionally equipped with a unit for sending the probe beam image simultaneously to all said photodetectors, a synchronizing unit and a time delay unit, connected with one another and with the pump laser unit, the probe beam forming unit and the registration unit.

19. The apparatus of claim 18 wherein the unit for sending the probe beam image is a system of semi-conducting mirrors to shift (split) the probe beam.

20. The apparatus of claim 18 wherein the unit for sending the probe beam image is a switching unit for consecutive spatial shift of said photodetectors.

21. The apparatus of claim 15 wherein a system of splitting the pump laser beam to the main one and the additional one is introduced on the way of the pump beam formed by the pump pulse laser, an optical delay line being introduced on the way of the additional beam, said line being connected with the time delay unit to form a probe beam.

22. The apparatus of claim 18 wherein the probe beam-forming unit is a continuous laser connected with the synchronizing unit.

23. The apparatus of claim 18 wherein the probe beam-forming unit is a pulse laser connected with the time delay unit.

24. The apparatus of claim 18 being additionally equipped with the unit for turning the probe beam as related to the sample observed, or with the unit for turning the sample itself, connected with the synchronizing unit and with the registration unit.

25. The apparatus of claim 18 being additionally equipped with the image-processing unit connected with said photodetectors, the synchronizing unit, and the time delay unit.

26. The apparatus of claim 18 being additionally equipped with the pump beam wavelength-changing unit connected with the pump laser unit.

27. The apparatus of claim 18 comprising a pump beam intensity-modulator on the way of the pump beam, and a synchronous detecting unit connected with the outlet of a photodetector or photodetectors used to register the probe beam, the modulator being connected with the synchronous detecting unit.

28. The apparatus of claim 18 comprising a high-sensitive infrared photodetector connected with the registration unit, and an additional infrared optical system located between the sample and said infrared photodetector.

29. The apparatus of claim 18 comprising a high-speed acoustic sensing element attached to the sample and connected with the registration unit.

* * * * *